United States Patent
Bourgelas et al.

(10) Patent No.: US 8,310,229 B2
(45) Date of Patent: Nov. 13, 2012

(54) INTELLIGENT EDDY CURRENT ARRAY PROBE WITH EMBEDDED FIRING SEQUENCE MEMORY

(75) Inventors: Tommy Bourgelas, Québec (CA); Benoit Lepage, Québec (CA)

(73) Assignee: Olympus NDT, Waltham, MA (US)

( * ) Notice: Subject to any disclaimer, the term of this patent is extended or adjusted under 35 U.S.C. 154(b) by 500 days.

(21) Appl. No.: 12/410,635

(22) Filed: Mar. 25, 2009

(65) Prior Publication Data

US 2009/0243605 A1  Oct. 1, 2009

Related U.S. Application Data

(60) Provisional application No. 61/039,471, filed on Mar. 26, 2008.

(51) Int. Cl.
*G01N 27/82* (2006.01)
(52) U.S. Cl. .......... 324/240; 324/242; 324/243
(58) Field of Classification Search ........ 324/222, 324/227–228, 232, 239–243
See application file for complete search history.

(56) References Cited

U.S. PATENT DOCUMENTS

| | | | | |
|---|---|---|---|---|
| 5,047,719 A | * | 9/1991 | Johnson et al. | 324/242 |
| 6,119,245 A | * | 9/2000 | Hiratsuka | 714/6.11 |
| 6,791,319 B2 | * | 9/2004 | Hiroshima | 324/240 |
| 6,914,427 B2 | * | 7/2005 | Gifford et al. | 324/242 |
| 7,385,392 B2 | * | 6/2008 | Schlicker et al. | 324/242 |
| 7,560,920 B1 | * | 7/2009 | Ouyang et al. | 324/242 |
| 2008/0040449 A1 | * | 2/2008 | Grant et al. | 709/218 |
| 2008/0052936 A1 | * | 3/2008 | Briggs et al. | 33/502 |
| 2009/0115410 A1 | * | 5/2009 | McKnight et al. | 324/240 |

* cited by examiner

*Primary Examiner* — Arleen M Vazquez
(74) *Attorney, Agent, or Firm* — Ostrolenk Faber LLP

(57) ABSTRACT

An intelligent eddy current array probe comprising a plurality of coil elements and an embedded non-volatile memory element is disclosed. Prior to coupling the intelligent eddy current array probe to an NDI system, a data table describing a desired firing sequence for the array probe within a given inspection operation is created. This data table is then stored within the embedded non-volatile memory element of the intelligent eddy current array probe such that when the array probe is coupled to the NDI system, the elements of the NDI system can load and execute the stored firing sequence without operator intervention. In this way, a plurality of intelligent eddy current array probes, each with its own firing sequence, can be used interchangeably within a single NDI system without the need for mechanical adjustments to the NDI system.

14 Claims, 5 Drawing Sheets

|        | RETURN ENABLE FIELD | SEND ENABLE FIELD |
|--------|---------------------|-------------------|
| Bit 11 | DRIVE/RX BLOCK 11 RETURN ENABLE | DRIVE/RX BLOCK 11 SEND ENABLE |
| Bit 10 | DRIVE/RX BLOCK 10 RETURN ENABLE | DRIVE/RX BLOCK 10 SEND ENABLE |
| Bit 9  | DRIVE/RX BLOCK 9 RETURN ENABLE  | DRIVE/RX BLOCK 9 SEND ENABLE  |
| Bit 8  | DRIVE/RX BLOCK 8 RETURN ENABLE  | DRIVE/RX BLOCK 8 SEND ENABLE  |
| Bit 7  | DRIVE/RX BLOCK 7 RETURN ENABLE  | DRIVE/RX BLOCK 7 SEND ENABLE  |
| Bit 6  | DRIVE/RX BLOCK 6 RETURN ENABLE  | DRIVE/RX BLOCK 6 SEND ENABLE  |
| Bit 5  | DRIVE/RX BLOCK 5 RETURN ENABLE  | DRIVE/RX BLOCK 5 SEND ENABLE  |
| Bit 4  | DRIVE/RX BLOCK 4 RETURN ENABLE  | DRIVE/RX BLOCK 4 SEND ENABLE  |
| Bit 3  | DRIVE/RX BLOCK 3 RETURN ENABLE  | DRIVE/RX BLOCK 3 SEND ENABLE  |
| Bit 2  | DRIVE/RX BLOCK 2 RETURN ENABLE  | DRIVE/RX BLOCK 2 SEND ENABLE  |
| Bit 1  | DRIVE/RX BLOCK 1 RETURN ENABLE  | DRIVE/RX BLOCK 1 SEND ENABLE  |
| Bit 0  | DRIVE/RX BLOCK 0 RETURN ENABLE  | DRIVE/RX BLOCK 0 SEND ENABLE  | b'0 = ISOLATE COIL FROM INSTRUMENT
b'1 = COUPLE COIL TO INSTRUMENT

FIG. 3B

|                  | RETURN GAIN FIELD |
|------------------|-------------------|
| Bits 22 and 23   | DRIVE/RX BLOCK 11 RETURN GAIN SETTING |
| Bits 20 and 21   | DRIVE/RX BLOCK 10 RETURN GAIN SETTING |
| Bits 18 and 19   | DRIVE/RX BLOCK 9 RETURN GAIN SETTING  |
| Bits 16 and 17   | DRIVE/RX BLOCK 8 RETURN GAIN SETTING  |
| Bits 14 and 15   | DRIVE/RX BLOCK 7 RETURN GAIN SETTING  |
| Bits 12 and 13   | DRIVE/RX BLOCK 6 RETURN GAIN SETTING  |
| Bits 10 and 11   | DRIVE/RX BLOCK 5 RETURN GAIN SETTING  |
| Bits 8 and 9     | DRIVE/RX BLOCK 4 RETURN GAIN SETTING  |
| Bits 6 and 7     | DRIVE/RX BLOCK 3 RETURN GAIN SETTING  |
| Bits 4 and 5     | DRIVE/RX BLOCK 2 RETURN GAIN SETTING  |
| Bits 2 and 3     | DRIVE/RX BLOCK 1 RETURN GAIN SETTING  |
| Bits 0 and 1     | DRIVE/RX BLOCK 0 RETURN GAIN SETTING  | b'11 = Gain Level #4 (highest)
b'10 = Gain Level #3
b'01 = Gain Level #2
b'00 = Gain Level #1 (lowest)

FIG. 3C

INTELLIGENT EDDY CURRENT ARRAY PROBE WITH EMBEDDED FIRING SEQUENCE MEMORY

CROSS REFERENCE TO RELATED APPLICATIONS

This application claims the benefit and priority of U.S. Provisional patent application Ser. No. 61/039,471, filed Mar. 26, 2008 entitled AN INTELLIGENT EDDY CURRENT ARRAY PROBE WITH EMBEDDED FIRING SEQUENCE MEMORY, the entire disclosure of which is incorporated herein by reference.

BACKGROUND OF THE INVENTION

The present invention relates to non-destructive inspection (NDI) instruments, and more particularly to an intelligent eddy current array probe which contains an embedded memory storage element for storing probe specific firing sequence information and transmitting the same to an NDI system upon connection of said array probe.

Any discussion of the related art throughout this specification should in no way be considered as an admission that such art is widely known or forms a part of the common general knowledge in the field.

Eddy current inspection is a well known NDI technique used to examine conductive materials. In a typical eddy current inspection operation, an eddy current array probe, comprising a plurality of coils, is placed adjacent to the surface of a material under inspection. At the start of an inspection operation, an NDI instrument coupled to said eddy current array probe energizes one or more coils within the array. This, in turn, induces a current in the material under inspection. One or more coils within the probe array then sense this induced current and provide a measurement signal to the NDI instrument. By measuring the current induced in a material under inspection, the impedance of said material can be calculated. Further, by tracking the impedance of a material under inspection as the probe is moved along the surface of said material (or, in some NDI operations, comparing the measured impedance to that of a stored reference), flaws and defects within said material can be found and analyzed.

In many advanced eddy current inspection operations, the individual coils of an eddy current array probe are energized and sensed in a specific sequence. This sequence, commonly referred to as a firing sequence, improves the efficiency and quality of an eddy current inspection. Typically, an NDI eddy current instrument will have a limited number of generator elements (used to energize the coils of the array probe) and a limited number of receiver elements (used to measure the induced currents sensed by the coils of the array probe). As such, an eddy current inspection operation making use of a firing sequence typically uses a multiplexer unit situated between an NDI instrument and an array probe to couple and decouple the individual coils of said array probe to the generator and receiver elements within said NDI instrument in accordance with the needs of a firing sequence devised for a given inspection operation.

An inspection operation on a cylindrical test piece, for example, would typically use an eddy current array probe with coils arranged circumferentially in a ring about said test piece. The firing sequence for such an inspection operation is directly dependent on the number of coils within the eddy current array probe being used to evaluate the tube. As different diameter test pieces are inspected, different eddy current array probes—with differing numbers of coils arranged in rings of differing diameters—are used such that the inspection operation can be optimized. Within such an inspection operation, each eddy current array probe used with the NDI system will require that the NDI instrument—or, in the case of some more advanced NDI systems, the programmable multiplexer used to couple the array probe to the NDI instrument—be prepared with a specific firing sequence optimized for that probe.

In prior art systems, preparing such an NDI system with a probe specific firing sequence requires that an additional step be performed when switching between different eddy current array probes. Such secondary steps include, but are not limited to, manually entering a new firing sequence algorithm into the system, adjusting connections between the instrument or multiplexer and the array probe by using different cablings, connector adapters, and the like, or wiring in different hardware components (such as a multiplexer specifically designed to function with a specific array probe and a specific inspection operation). These additional steps within an NDI operation can often be tedious, time consuming, require additional hardware to be available, negatively affect NDI system reliability, and introduce opportunities for error within said inspection operation.

Accordingly, it would be advantageous to provide an eddy current array probe for an NDI operation which did not require that a probe specific firing sequence be manually entered into the system by an operator.

SUMMARY OF THE DISCLOSURE

It is the object of the present disclosure to overcome the problems associated with prior art. This is attained by introducing the intelligent eddy current array probe of the present disclosure. The intelligent eddy current array probe of the present disclosure contains an embedded non-volatile memory element which is used to store a data table describing a firing sequence specific to said eddy current array probe and the non-destructive inspection (NDI) inspection operation for which it is intended. When coupled to an instrument or multiplexer in an NDI system, this data table can be accessed through a memory interface and loaded into the NDI system automatically and without operator intervention.

In the preferred embodiment of the present disclosure, the memory interface provides a means for the embedded non-volatile memory element to be programmed and reprogrammed with firing sequence information through a personal computer. In an alternate embodiment, a specially designed NDI instrument can be used to edit and store firing sequence data tables within the embedded non-volatile memory element, providing greater flexibility for updates to the firing sequence information.

In the preferred embodiment of the present disclosure, the memory interface takes the form of an industry standard hardwired parallel memory interface. However, any industry standard memory protocols which allow data to be transferred from the probe to other elements within the NDI system are suitable for use with the methods of the present disclosure. Such protocols include, but are not limited to, one wire communication protocols, wireless or RF protocols, and older serial interface standards such as, but not limited to, RS-232.

Accordingly it is the object of the present disclosure to provide an intelligent eddy current array probe for use within an NDI operation.

It is also an object of the present disclosure that this intelligent eddy current array probe contain an embedded non-volatile memory element which is used to store a firing sequence data table specific to the requirements of the array probe and the inspection operation for which the probe is intended.

It is further an object of the present disclosure that this intelligent eddy current array probe have means to interface with an external system such as, but not limited to, a personal computer or a specially designed NDI instrument, such that said external system have means to store a data table describing probe specific firing sequence information within the embedded non-volatile memory device.

It is also an object of the present disclosure that this intelligent eddy current array probe have means to load the firing sequence data table stored within the embedded memory element into the components of an NDI system automatically upon connection to said NDI system.

Other features and advantages of the present invention will become apparent from the following description of the invention that refers to the accompanying drawings.

BRIEF DESCRIPTION OF THE DRAWINGS

FIG. 3B is a table detailing the meaning of the bit values of the RETURN ENABLE and SEND ENABLE fields in the exemplary data table of FIG. 3A;

FIG. 3C is a table detailing the meaning of the bit values within the RETURN GAIN field in the exemplary data table of FIG. 3A;

DETAILED DESCRIPTION

Figure 1A:
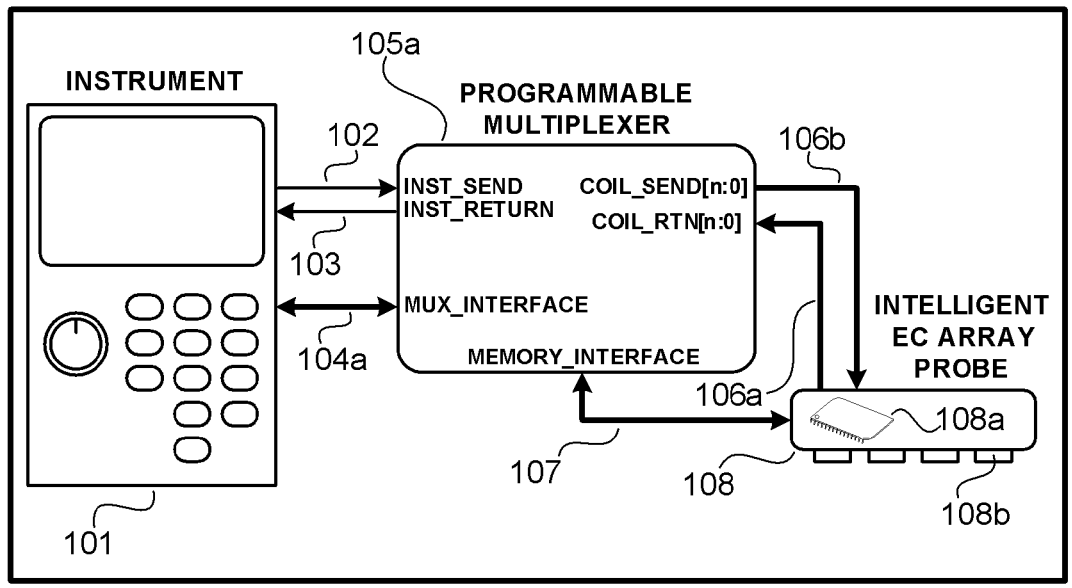
FIG. 1A is a block diagram of a first exemplary eddy current inspection system using the intelligent eddy current array probe of the present disclosure.

FIG. 1A is a block diagram illustrating a first exemplary non-destructive inspection (NDI) eddy current system using the intelligent eddy current array probe of the present disclosure 108. An NDI eddy current instrument 101 provides an INST_SEND signal 102 (the excitation signal used to drive the one or more coils used to induce a test current in a material under inspection) to and receives an INST_RETURN signal 103 (the measurement signal from the one or more coils used to sense said induced current within a material under inspection) from a programmable multiplexer 105a. A control interface 104a is provided between the instrument 101 and the programmable multiplexer 105a such that the instrument 101 can direct the programmable multiplexer 105a to make the necessary connections required for the different time slots within the firing sequence being employed in a given inspection operation. The design and operation of such a multiplexer circuit (both programmable or non-programmable) suitable for making such connections between the individual elements of an array probe and an NDI instrument is well known to those skilled in the art.

A plurality of connections is made between the programmable multiplexer 105a and the intelligent eddy current array probe 108. A first group of connections, COIL_SEND[n:0] 106b, provides the programmable multiplexer 105a with means to drive each of the individual coils 108a of the array probe 108 with the excitation signal (INST_SEND 102) provided by the NDI instrument 101. A second group of connections, COIL_RTN[n:0] 106a, provides the programmable multiplexer with means to return measurement signals sensed by the individual coils 108b of the array probe 108 to the NDI instrument's 101 receiver input, INST_RETURN 103. A memory interface 107 is also provided between the programmable multiplexer 105a and the array probe 108 to provide the programmable multiplexer 105a with means to access and read in a probe specific firing sequence data table stored within the array probe 108 prior to the start of the inspection operation.

By using a programmable multiplexer 105a in the NDI system of FIG. 1, the multiplexer interface, MUX_INTERFACE 104a, is significantly simplified, as the programmable multiplexer 105a will comprise the means to execute the plurality of interconnections during each time slot as described by the loaded firing sequence data table. For a system using a non-programmable multiplexer, however, the bulk of this interconnection and switching logic will reside within the instrument, and as such, the memory interface 107 will be required to couple directly between the array probe 108 and the NDI instrument 101.

Figure 1B:
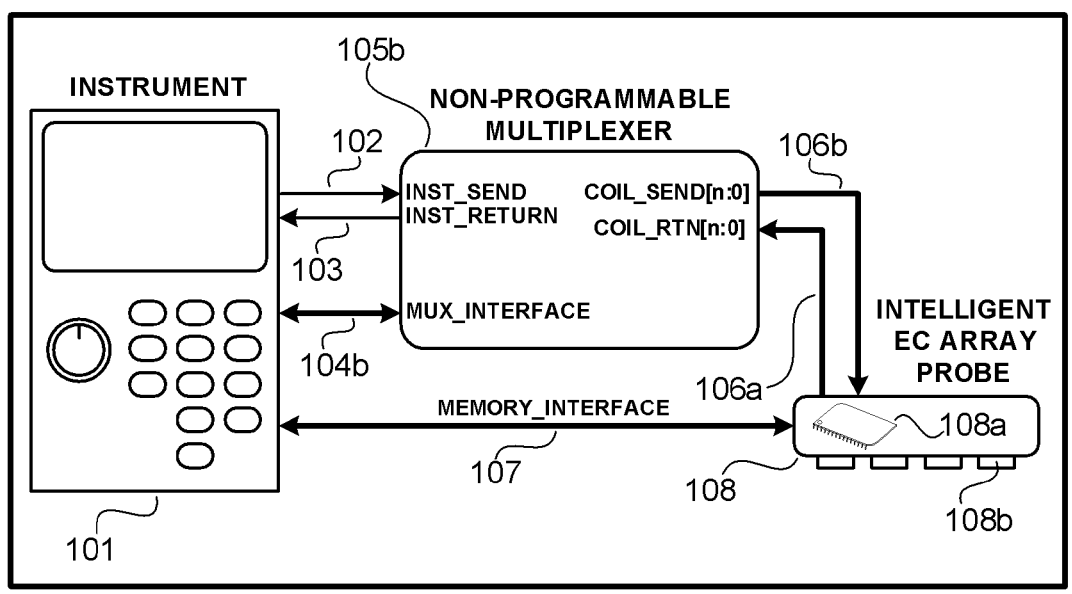
FIG. 1B is a block diagram of a second exemplary eddy current inspection system using the intelligent eddy current array probe of the present disclosure.

FIG. 1B is a block diagram of a second exemplary NDI system using the intelligent eddy current array probe of the present disclosure with a non-programmable multiplexer 105b. Within this system, the memory interface 107 couples directly between the array probe 108 and the NDI instrument 101. When the array probe is first connected in this second exemplary system, the NDI instrument 101 accesses and reads in the firing sequence data table stored within the non-volatile memory element 108a through the memory interface 107. Using the more complex multiplexer interface 104b, the NDI instrument 101 then directs the non-programmable multiplexer 105b to make the instrument/coil interconnections described by the firing sequence data table for each time slot.

Figure 1C:
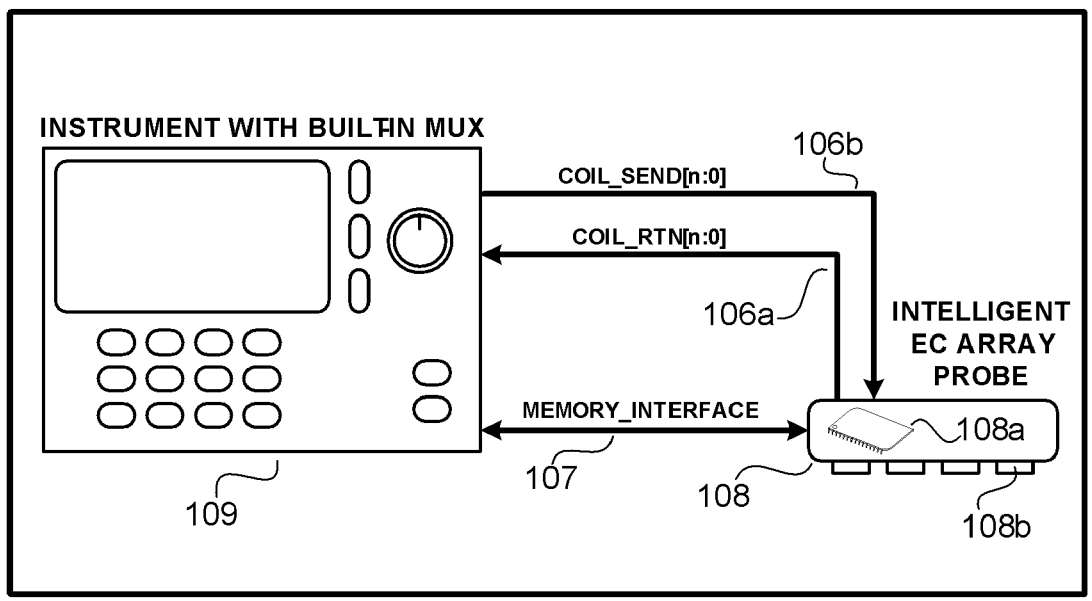
FIG. 1C is a block diagram of a third exemplary eddy current inspection system using the intelligent eddy current array probe of the present disclosure.

FIG. 1C is a block diagram of a third exemplary NDI system using the intelligent eddy current array probe of the present disclosure 108 with a more complex NDI instrument 109, said instrument including internal multiplexing circuitry. As in the second exemplary NDI system detailed in FIG. 1B, within the third exemplary NDI system the memory interface 107 couples directly between the array probe 108 and the NDI instrument 109. In this system, the NDI instrument 109 also couples directly to the individual coils of the array probe 108 by way of a first group of connections, COIL_SEND[n:0] 106b (used to provide an excitation signal to the individual coil elements 108b of the array probe 108) and a second group of connections COIL_RTN[n:0] 106a (used to provide the signals sensed by the individual coils 108b of the array probe 108 to the NDI instrument 109). When the array probe 108 is first connected in this third exemplary system, the NDI instrument 109 accesses and reads in the firing sequence data table stored within the non-volatile memory element 108a through the memory interface 107. The NDI instrument 109 then makes use of its internal multiplexing circuitry and logic to provide the necessary connections required for the different time slots of the firing sequence according to the loaded data table.

The intelligent eddy current array probe of the present disclosure 108 is comprised of an array of coil elements 108b and an embedded non-volatile memory element 108a. Prior to the eddy current array probe's 108 connection to an NDI system, the embedded non-volatile memory element 108a is loaded with a data table describing the desired firing sequence which will be used with the array probe 108 for a specific inspection operation. When the array probe 108 is first connected to the NDI system, the memory interface 107 automatically loads the data table stored within the embedded non-volatile memory element 108a into its sequencing circuitry. In this way, a desired firing sequence—optimized for the eddy current array probe 108 and the specific inspection operation—stored within the non-volatile memory element 108a can be accessed by and prepared for use within an NDI system.

The firing sequence data table stored within the non-volatile memory element 108a describes—in a way easily interpreted and executed by the elements of the NDI system—the interconnections required between the excitation signal (INST_SEND 102) provided by the NDI instrument 101 and the individual coil elements 108b, as well as the interconnections required between the individual coil elements 108b and the INST_RETURN signal 103 provided to the NDI instrument 101.

For some inspection operations, the firing sequence data table can also include multiplexer and NDI instrument specific parameter settings which vary from time slot to time slot during the firing sequence. Such parameters include, but are not limited to, gain settings for the individual measurement signals sensed by the individual coil elements 108b and a selection control for inspection operations wherein an NDI instrument provides more than one excitation signal, said excitation signals differing, for example, in frequency or amplitude.

In the preferred embodiment of the present disclosure, this data table is prepared on a personal computer and stored within the non-volatile memory element embedded within the intelligent eddy current array probe of the present disclosure. This firing sequence data table can be created with a plurality of software tools running on said personal computer, such as, but not limited to, a custom software program (provided, for example, by the manufacturer of the array probe), a spreadsheet program such as Microsoft Excel, or a simple text editor.

In an alternate embodiment of the present disclosure, special software is loaded onto an NDI instrument which provides said instrument with means to create and edit firing sequence data tables and further load said data tables directly onto the intelligent eddy current array probe of the present disclosure. Within this embodiment, the intelligent eddy current array probe can be easily reprogrammed in the field by a skilled operator, allowing said operator greater flexibility during an inspection operation while still preserving the benefits of the automated firing sequence data loading methods of the present disclosure during normal inspection operations.

Figure 2:
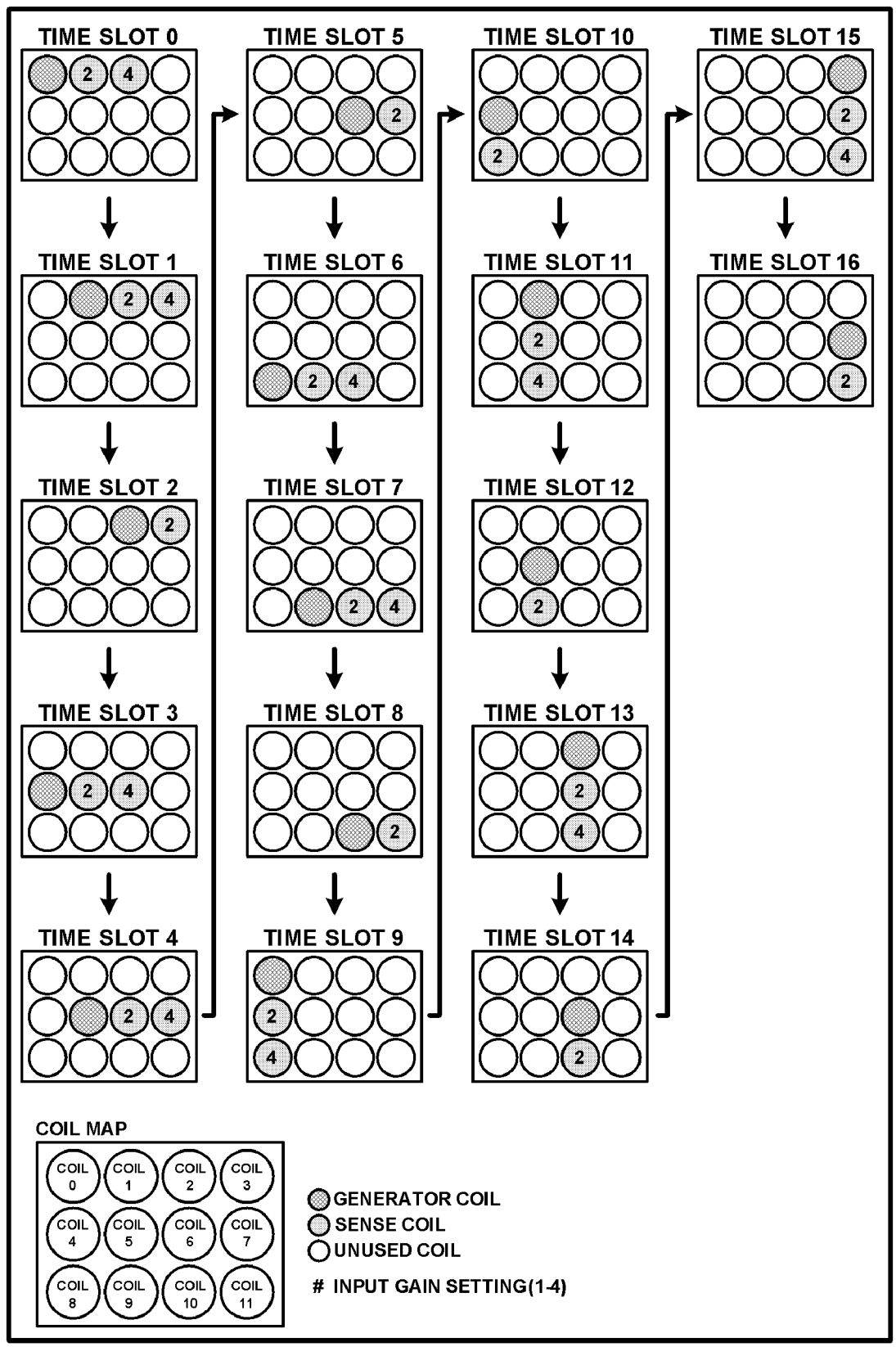
FIG. 2 is a diagram illustrating an exemplary firing sequence suitable for use with a twelve element eddy current array probe.

FIG. 2 is a time slot diagram which illustrates an exemplary firing sequence suitable for use on a twelve element eddy current array probe. The time slot diagram of FIG. 2 has been provided such that an exemplary data table suitable for use with the methods of the present disclosure can be introduced. It should be noted that within the time slot diagram of FIG. 2, those coils marked with crossing diagonal lines represent energized (or generator) coils, and those coils marked with a field of black dots represent measurement (or sense) coils. Those coils with no markings represent coils isolated from the NDI eddy current instrument. In this exemplary firing sequence, a gain value which should be applied to the measurement signal received from each of the sense coils during each time slot has been indicated by a small numeral within the coil itself These numerals range from one (1), the lowest gain setting, to four (4), the highest gain setting.

Figure 3A:
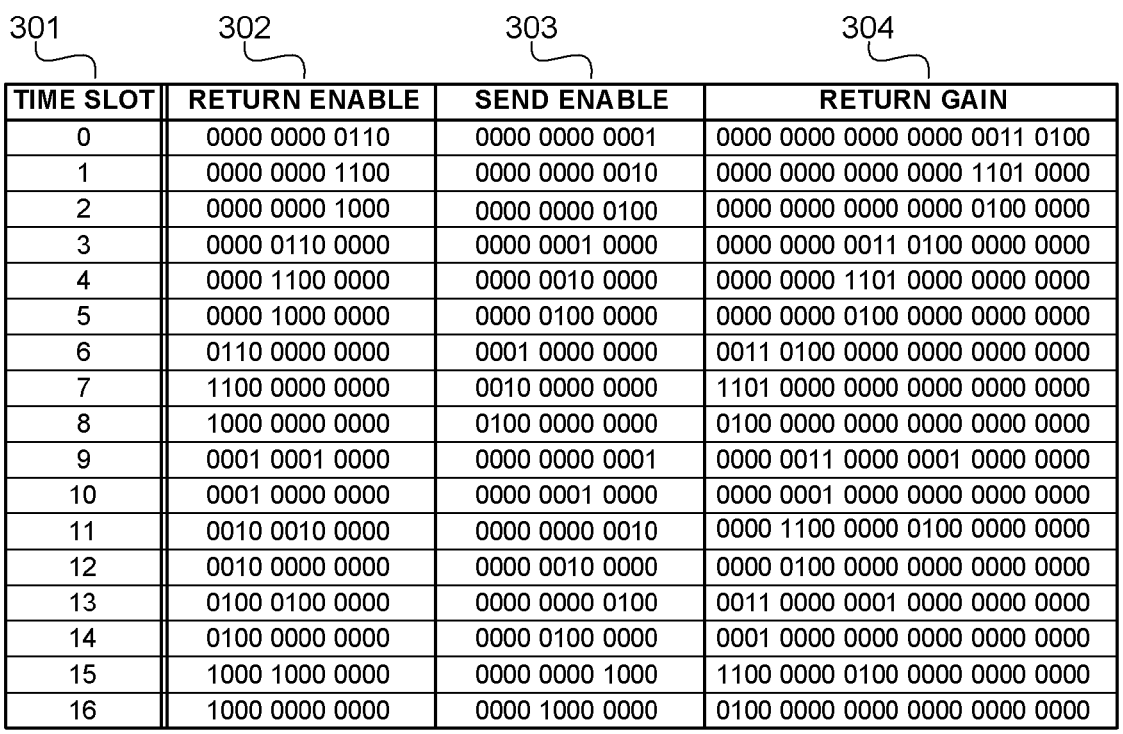
FIG. 3A is an exemplary data table describing the firing sequence shown in FIG. 2 in accordance with the methods of the present disclosure.

FIG. 3A is a firing sequence data table describing the firing sequence shown in FIG. 2. The data shown in this table would be first—prior to connection with an NDI system—stored within and later—upon connection with an NDI system— loaded from the non-volatile memory element (108a in FIGS. 1A and 1B) of the intelligent eddy current array probe of the present disclosure (108 in FIGS. 1A and 1B). It should be noted that the exemplary firing sequence shown in FIG. 2 and described by the data table of FIG. 3A has been constructed to drive a twelve element eddy current array probe. As such, the data table of FIG. 3A includes interconnection and gain information for exactly twelve elements (coils).

The table in FIG. 3A contains four columns. The TIME SLOT column 301 simply enumerates the seventeen time slots in the firing sequence. The RETURN ENABLE column 302 lists a twelve bit binary number representing how each of the twelve coils should be coupled to the receiver channel provided to the NDI instrument, INST_RETURN (103 in FIGS. 1A and 1B), during each time slot. A binary value of one (b'1) corresponds to coupling said receiver channel to a coil for a given time slot, and, conversely, a binary value of zero (b'0) corresponds to isolating said receiver channel from a coil for a given time slot.

Similarly, the SEND ENABLE column 303 lists a twelve bit binary number representing how each of the twelve coils should be coupled to the energizing signal provided by the NDI instrument, INST_SEND (102 in FIGS. 1A and 1B), during each time slot. A binary value of one (b'1) corresponds to coupling a coil to said energizing signal for a given time slot, and, conversely, a binary value of zero (b'0) corresponds to isolating a coil from said energizing signal for a given time slot. For clarity, the mapping of each bit within these two fields as they apply to each coil within the exemplary twelve element array probe has been explicitly detailed within the table of FIG. 3B.

Finally, the RETURN GAIN column 304 lists a twenty-four bit number (two bits for each coil used in this exemplary firing sequence) representing the gain which should be applied to the measurement signal sensed by each of the twelve coils during each time slot. For clarity, the mapping of each bit in this field has been explicitly detailed in FIG. 3C.

It should be noted that although FIG. 3A shows an exemplary data table format and structure suitable to represent the firing sequence of FIG. 2, the present disclosure is not limited in this regard. Indeed, it is well known to those skilled in the art that a plurality of data representations, so-called look up table formats, and the like exist and could be used with the methods of the present disclosure to efficiently represent the array of control signals required to produce a firing sequence such as is shown in FIG. 2. As such, the data table of FIG. 3A has been included to represent this plurality of data representation methods by way of a clear and concise example.

While the preferred embodiment of the present disclosure describes using the non-volatile memory element (108a in FIGS. 1A-1C) within the intelligent eddy current array probe to store a firing sequence data table describing the interconnections, gain settings, and the like required for a specific inspection operation, an alternate method is also contemplated. In an alternate embodiment, the non-volatile memory element within the intelligent eddy current array probe stores a probe identification value, such as, but not limited to, a unique serial number for said probe, a model number, or an predetermined operation number. This identification value, automatically read in by an NDI system when a probe is coupled to said system, is then used to select a firing sequence data table from a plurality of such data tables stored within the NDI system. In this way, the methods of the present invention are realized while minimizing the amount of data stored within the intelligent eddy current array probe and transferred via the memory interface.

Although the present invention has been described in relation to particular embodiments thereof, many other variations and modifications and other uses will become apparent to those skilled in the art. It is preferred, therefore, that the present invention not be limited by the specific disclosure herein.

What is claimed is:

1. An eddy current array probe, comprising:
   a plurality of coils selectively operable as either generator coils or as sense coils, wherein the passage of a current through a generator coil is effective to induce eddy currents in a test object to thereby enable one or more of the sense coils to sense the eddy current;
   a signal processing element, which enables receipt of an excitation signal for the generator coils and which is operable to output a return signal from the sense coils; and
   a memory embedded in the array probe for storing a configuration of the coils as generator and sense coils for a plurality of time slots,
   wherein the memory is readable by the signal processing element to produce a firing sequence for the coils during the time slots, wherein the firing sequence includes a configuration for the coils enabling any coil or any number of coils to be configured as generator coils; and any other coil or any number of the coils to be configured as sense coils at any given time slot; and each coil to be operated with individual parameter settings;
   wherein, further in combination with an instrument operable and controllable by an operator, the signal processing element is coupled with the instrument, wherein the probe is configured to be selectively electronically coupled to, or separated from the instrument;
   wherein, the signal processing element is configured to provide to the memory the firing sequence,
   wherein the memory is readable and configured to be reprogrammed by the instrument.

2. The array probe of claim 1, wherein the memory is a non-volatile, reprogrammable memory.

3. The array probe of claim 2, the signal processing element includes a multiplexer to provide the excitation signal to selected generator coils during the successive time slots and to receive the return signal from the sense coils.

4. The array probe of claim 3, wherein the multiplexer is provided in a housing, separate from a housing associated with the instrument.

5. The array probe of claim 3, wherein the coils are arranged in a matrix containing up to 64 coils.

6. The array probe of claim 3, wherein the memory is sufficient to provide a coil configuration for up to thirty-two time slots.

7. The array probe of claim 3, further including a parallel memory interface.

8. The array probe of claim 2, wherein the memory is further operable to store gain settings for the sense coils.

9. The array probe of claim 1, wherein the instrument comprises a menu of various firing sequences for different applications and including a facility for altering the contents of the memory of the array probe to configure the same for different applications.

10. The probe of claim 1, wherein the individual settings of operational parameters include the settings for gain, frequency and amplitude.

11. A method of testing an object using an eddy current instrument having an eddy current array probe, the method comprising the steps of:
    providing an array probe having a plurality of coils selectively operable as either generator coils or as sense coils, wherein the passage of a current through a generator coil is effective to induce eddy currents in the object to thereby enable one or more sense coils to sense the eddy currents;
    storing in a memory embedded in the array probe a firing sequence of the coils as either generator or sense coils for a plurality of time slots;
    wherein the firing sequence includes a configuration for the coils enabling any coil or any number of coils to be configured as generator coils; and an other coil or an number of the coils to be configured as sense coils at any given time slot and each coil to be operated with individual parameter settings;
    operating the array probe coils to test the object based on the stored configuration; and
    altering the contents of the memory by storing therein an alternate configuration for the coils and operating the array probe with the altered configuration of the coils;
    wherein the firing sequence and steps of storing, operating and altering are controlled by a signal processing element associated with the instrument and,
    wherein the memory is readable and capable of being reprogrammed by the instrument.

12. The method of claim 11, the signal processing element including utilizing a multiplexer to direct the excitation signal and to receive the return signal from the array probe.

13. The method of claim 12, further including an eddy current instrument which is coupled to the multiplexer and operable by a user to control the function of the array probe.

14. The method of claim 13, including utilizing the instrument to alter the contents of the memory of the array probe.

* * * * *